US006408681B1

(12) United States Patent
Gurton et al.

(10) Patent No.: US 6,408,681 B1
(45) Date of Patent: Jun. 25, 2002

(54) SINGLE PARTICLE PHOTOACOUSTIC ABSORPTION SPECTROMETER

(75) Inventors: Kristan P. Gurton, Silver Spring; James B. Gillespie, Ellicott City, both of MD (US)

(73) Assignee: The United States of America as represented by the Secretary of the Army, Washington, DC (US)

( * ) Notice: Subject to any disclaimer, the term of this patent is extended or adjusted under 35 U.S.C. 154(b) by 0 days.

(21) Appl. No.: 09/533,956

(22) Filed: Mar. 23, 2000

(51) Int. Cl.[7] .............................................. G01N 21/00
(52) U.S. Cl. ..................... 73/24.02; 73/24.03; 73/24.06
(58) Field of Search ............................. 73/24.02, 24.06, 73/24.03; 250/339.13

(56) References Cited

U.S. PATENT DOCUMENTS

| 4,594,004 A | * | 6/1986 | Ishida et al. ................ 73/24.03 |
| 5,616,826 A | * | 4/1997 | Pellaux et al. .............. 73/24.02 |

OTHER PUBLICATIONS

Allen, D.T. and Palen, E. "Recent Advances in Aerosol Analysis by Infrared Spectroscopy", Dec. 1989, vol. 20, No. 4, pp. 441–455.*
Precision of Light Scattering Techniques for Measuring Optical Parameters of Microspheres, A.K. Ray, A. Souyri, E. James Davis and Teresa M. Allen, Applied Optics/vol. 30, No. 27/20 Sep. 1991.
A Three–Axis Spherical Void Electrodynamics Levitator trap for Microparticle Experiements, S. Arnold, American Institute of Physics, 1991 (Dec.).
Spherical Void Electrodynamic Levitator, S. Arnold and L.M. Folan, American Institute of Physics, 1987 (Sep.).
Development of Spectrophones for CW and Pulsed Radiation Sources, Charles Bruce, Atmospheric Sciences Laboratory, Aug. 1976.
Midinfrared Optical Properties of Petroleum Oil Aerosols, K.P. Gurton and C.W. Bruce, ARL–TR–255, Aug. 1994.
Trans–Spectral Absorption and Scattering of Electromagnetic Radiation by Diesel Soot, Charles W. Bruce, Thor F. Stromberg, Kristan P. Gurton and J.B. Mozer, Applied Optics, vol. 30, No. 12 Apr. 20, 1991.

* cited by examiner

*Primary Examiner*—Hezron Williams
*Assistant Examiner*—Michael Cygan
(74) *Attorney, Agent, or Firm*—Paul S. Clohan, Jr.; Mark D. Kelly; William Randolph

(57) ABSTRACT

A single particle photoacoustic absorption spectrometer for directly measuring the absorption spectra for in situ individual aerosol type particles that is comprised of an electrodynamic trap capable of suspending a charged particle in free-space in a non-intrusive manner; a source of modulated monochromatic electromagnetic radiation, e.g., a laser, and an acoustic transducer/resonator for detecting/amplifying sound waves emitted by the irradiated particle. Depending on the characteristics of the particle, a certain fraction of the electromagnetic energy will be absorbed by the particle resulting in its rapid heating and cooling at the modulation frequency. The heat generated within the particle is rapidly transferred to the surrounding air resulting in a sound wave. The intensity of the sound wave is proportional the absorbed energy by the particle. The wavelength of the monochromatic electromagnetic source is then shifted slightly and the measurement is repeated until the desired absorption spectra are completely recorded.

12 Claims, 2 Drawing Sheets

FIG. 1

SINGLE PARTICLE PHOTOACOUSTIC ABSORPTION SPECTROMETER

1. BACKGROUND OF THE INVENTION a. Field of the Invention

This invention relates generally to single particle absorption spectrometry and more particularly to spectrometry in which a photoacoustic technique is used to measure the absorption spectra for a single aerosol particle.

b. Description of the Prior Art

The disclosures of all such publications referenced herein, in their entireties, are hereby expressly incorporated by reference in this application as if fully set forth, for purposes of indicating the background of the invention and illustrating the state of the art.

Recent experiences in the Gulf War and with the Sarin poisonous gas attack in a Japanese subway have demonstrated the susceptibility of both military and civilian personnel to chemical/biological aerosol attacks and the need to develop some type of early warning system. Current methods for real time biological aerosol detection attempt to exploit the relatively weak fluorescence phenomena inherent in all living materials, G. W. Faris, R. A. Copeland, "Spectrally Resolved Absolute Fluorescence Cross Section of B. Globigii and B. Cercus", Stanford Research Institute, Technical Report 2913, (1992). Unfortunately, measured fluorescent spectra are often quite broad and featureless, making species discrimination and/or identification nearly impossible. It has become apparent that additional criteria must be considered, i.e., electromagnet (EM) absorption, if effective identification schemes are to be developed. In addition, researchers have pointed out that for any biological warfare (BW) early warning detection method to be truly effective it must be able to detect biological particulate concentrations on the order of 10 bio-particles per liter of air. Currently, all known detection schemes require bio-particle concentrations several orders of magnitude greater than this minimum detection limit.

In order to solve this complex and detailed problem, detailed absorption spectra derived directly from in situ bioaerosols, preferably a single particle, is badly needed. Prior scientific studies involving EM absorption by aerosols have used a conventional photoacoustic approach in which an ensemble or distribution of aerosol particles were necessary to conduct the measurement, C. W. Bruce, "Development of Flow Through Spectrophones for CW and Pulsed Radiation Sources", ECOM Tech. Report No. 5802, p. 1–57, (1976); C. W. Bruce, K. P. Gurton, T. F. Stromberg, "Trans-Spectral Absorption and Scattering of Electromagnetic Radiation by Diesel Soot, " Applied Optics, 30, No. 12, pp. 1537–1546, (1991); and K. P. Gurton, C. W. Bruce, "Mid-infrared Optical Properties of Petroleum Oil Aerosols," Army Research Laboratory Technical Report, No. APL-TR-255, White Sands Missile Range, NM, pp.1–43, (1994). Trying to apply this conventional photoacoustic approach as a early warning detection method has two major drawbacks. First, measurements conducted on an ensemble distribution of bioaerosols severely mask detailed spectral content due to averaging effects over both size and orientation of the particles, thus rendering the measured absorption spectra as featureless as fluorescence, A. V. Jelinek, C. W. Bruce, "Extinction Spectra, of High Conductivity Fibrous Aerosols", J Appl. Physics, 78, 2675, (1995). Second, very high particle concentrations are necessary to achieve good signal-to-noise and operation at the 10 particle per liter criteria would not be feasible.

Because this apparatus/technique can detect absorption spectra from a single aerosol particle, it is uniquely suited for detection at extremely low aerosol densities, i.e., at or below the 10 particle per liter criteria.

Thus, to reiterate, to date there are no rapid, reliable, effective means to detect low concentrations of harmful bioaerosols, that could be used to warn populations at risk in sufficient time to take evasive measures. We believe the device proposed here could satisfy this need.

2. SUMMARY AND OBJECTS OF THE INVENTION

It is an object of this invention to develop a method and a device capable of:

1) producing the free-space levitation of a single aerosol type particle (via an electrodynamic particle trap) to permit detailed analysis and study of the absorption characteristics without the detrimental effects of ensemble averaging inherent using current techniques;

2) identification and discrimination of hazardous bioaerosols to enable rapid detection of and early warning against a variety of hazardous aerosols;

3) to obtain nonintrusive measurement of absorption spectra of an individual particle in situ, thus allowing for detection at very low aerosol densities.

These and other objects are satisfied, at least in part, by a single particle photoacoustic absorption spectrometer including a particle trap for suspending a charged particle in free-space in a non-intrusive manner; a source of a electromagnetic energy modulated at a convenient acoustic frequency (e.g., a tunable laser chopped at 1 kHz), for rapid heating and cooling of the particle at the same acoustic frequency that results in a compressional/sound wave whose intensity is directly proportional to the EM absorption by the particle at the laser frequency of interest; a very sensitive, highly directional microphone (e.g., miniature electret microphone) positioned to detect the acoustic signal emitted by the suspended particle and; a resonant cylindrical cavity to amplify the acoustic wave. Thus the present invention provides an efficient, simple and effective means of suspending a single aerosol type particle stationary in free-space so that thermal changes in the particle (induced by optical absorption of the irradiating source) can be measured via the resultant acoustic signal.

Still other objects, features and advantages of the invention will be set forth in part in the description which follows, and in part will become apparent to those skilled in the art upon examination of the following, or may be learned by practice of the invention. As will be realized, the invention is capable of other different embodiments and its several details are capable of modification in various, obvious aspects all without departing from the invention. Accordingly, the drawings and descriptions will be regarded as illustrative in nature and not restrictive.

3. BRIEF DESCRIPTION OF THE DRAWINGS

The foregoing objects and advantages of the present invention will be more fully understood from the following detailed description having reference to the appended drawings wherein:

FIG. 1 shows a side cut-away view of principal components of a preferred embodiment according to the invention of this application.

4. DETAILED DESCRIPTION OF PREFERRED EMBODIMENTS

Figure 1:
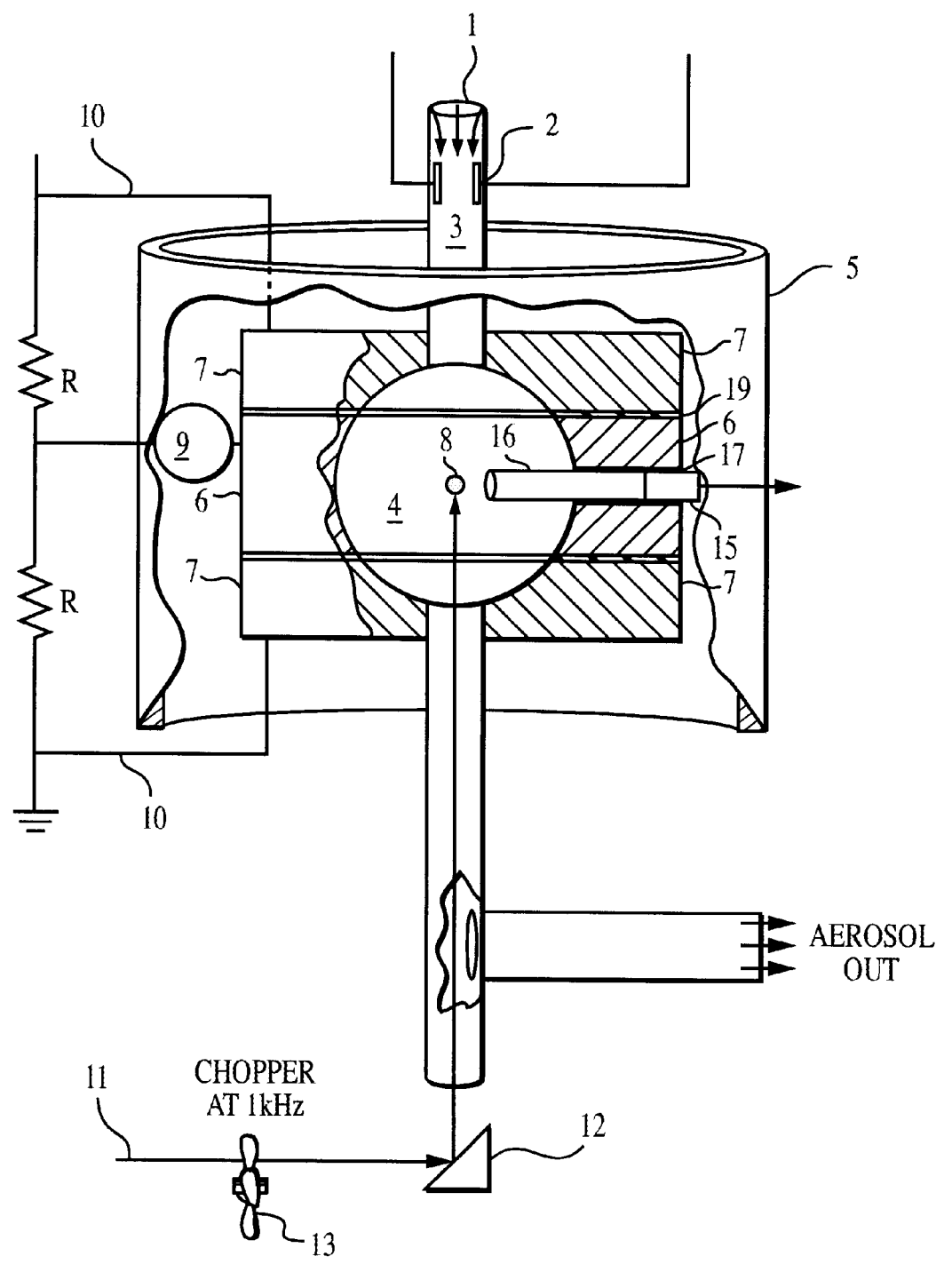
Figure 2:
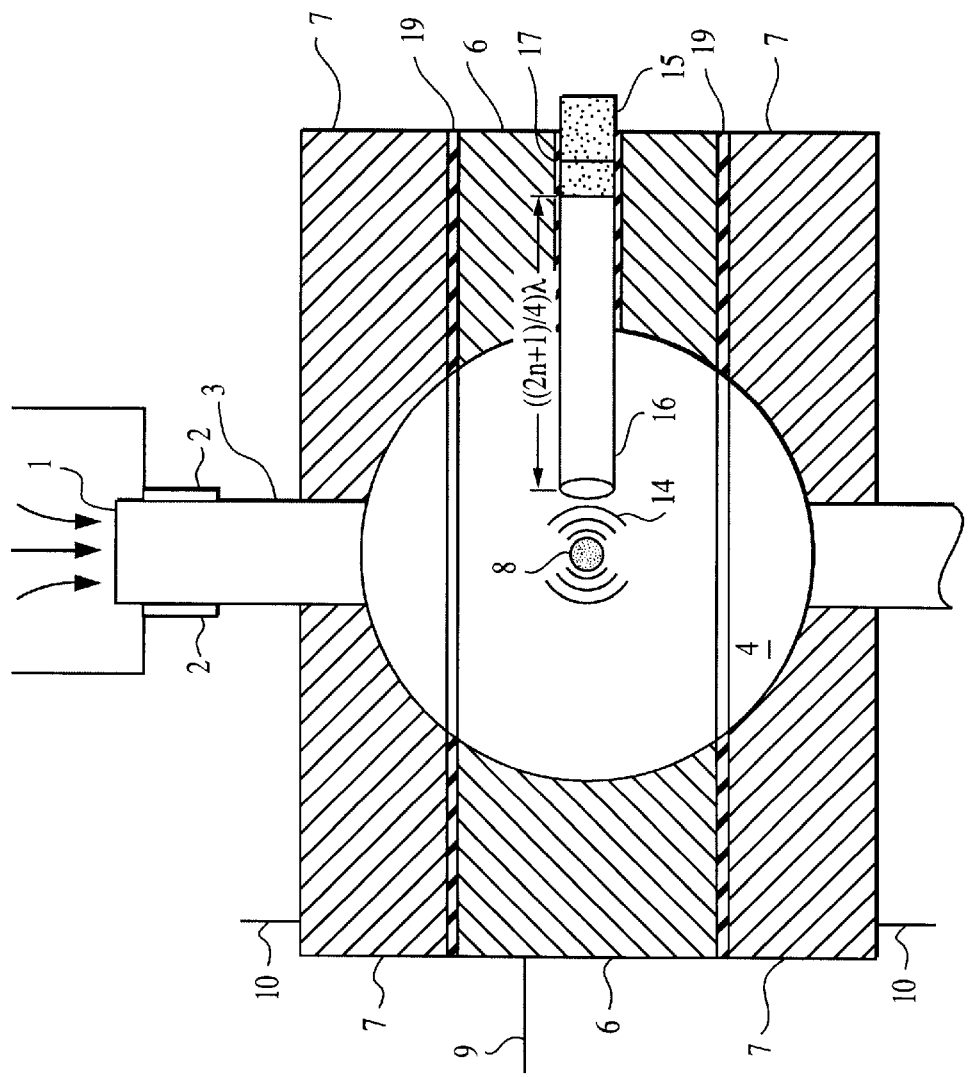
FIG. 2 shows a side cut-away view of principal components of the acoustic transducer/resonant structure necessary to amplify the acoustic signal according to a preferred embodiment.

As can be seen in FIGS. 1 and 2 ambient air containing unknown particulates are gently drawn into aerosol inlet 1 through a region or high electric potential 2 that is created via an anode/cathode combination, thus inducing an electrostatic charge on the particle(s). A DC potential of about 40 volts is sufficient to induce a net charge on the particle(s). The electrically charged aerosol is drawn through inlet tube 3 which extends vertically downward into electrodynamic spherical void particle trap 4. Although spherical void electrodynamic trap 4 is shown, a variety of electrodynamic trap geometries suitable for use in the present invention might also suffice, e.g., hyperbolic, ring, parallel plate, etc., and would be familiar to those of ordinary skill in the art, S. Arnold, "A Three-axis spherical void electrodynamic levitator trap for microparticle experiments", Rev. Sci. Instrum., 62, 3025, (1991); A. K. Ray, A. Souyri, E. J. Davis, "Precision of light scattering techniques for measuring optical parameters of microspheres", Appl. Opt.30, no.27, 3974, (1991). Spherical-void electrodynamic trap 4 is surrounded by acoustic damping material 5. The amount of sound insulation required will of course depend on the ambient noise in the environment in which the trap will be used.

A good discussion of the basic operation of electrodynamic aerosol traps may be found in the book Optical Effects Associated With Small Particles, Barber, P. W., Chang, R. K., World Scientific Press, New York, 1989, incorporated herein by reference for background purposes. Basically, particles of a selected charge to mass ratio are held within a region of the trap in which the electric field potential is zero. For the spherical void geometry shown, this zero potential point corresponds to the exact center of the sphere. It is a property of this "null" field point that a particle is stably trapped only under certain conditions, which depend on the charge to mass ratio, the physical dimensions of the trap, the amplitude and frequency of an AC induced field (applied to the conductive center portion 6 of the sphere), and a DC induced field created by applying a large voltage 10 across the two conductive end caps, 7 e.g., 100V. As shown in FIG. 1 a conductive center region 6 is electrically insulated from end cap regions 7 by a sheet of Teflon 19.

FIGS. 1 and 2 show single levitated charged particle 8 suspended in the center of particle trap 4. Initially, only the AC induced field is applied. As the charged particle 8 falls into the spherical void it is captured within the AC field and orbits in a lissajous type pattern. A DC voltage 10 is then applied across end caps 7 and the particle motion becomes linear. The DC voltage 10 is then set to an equilibrium value such that charged particle 8 remains stationary at the exact center of the void. In a preferred embodiment, the AC voltage source 9 is approximately 600 volts.

Next, a monochromatic light source 11 is directed to the center of the trap in order to illuminate the levitated particle 8 via a steering mirror 12. While a wavelength tunable laser source is used in a preferred embodiment, a band-pass "filtered" lamp source would also work. The intensity of light source 11 is modulated by an optical chopper 13 at a convenient acoustic frequency, e.g., 1 kHz. It is important that the beam from light source be tightly focused on the area where the particle is suspended so that maximum power is directed at the particle 8. A certain fraction of the energy of beam 11 will be rapidly absorbed by the particle 8 during the time in which the laser beam is open, resulting in the heating of the particle. Similarly, the converse is true when the beam is blocked, i.e., the particle will rapidly cool. This rapid heat and cooling from the absorbing particle 8 is transferred to the surrounding air and results in a radially outgoing acoustic wave 14, as shown in FIG. 2. The acoustic signal emitted from the particle is detected by a very sensitive electret microphone 15 mounted on the end of a cylindrical acoustic resonator 16 and is variably positioned through the circumference of the center portion of particle trap 4. The electret microphone is electrically isolated from the induced AC field 9 by a shielding conduit 17 as is shown in FIG. 2. In order to be resonantly "tuned", the length of the resonator tube 16 is trimmed to coincide with odd multiple quarter wavelengths of the modulation frequency, i.e., $((2n+1)/4)\lambda$, where n represents any positive whole number, $\lambda=v/f$, v is the speed of sound in air, and f is the modulation frequency of the chopper. For example, at a modulation frequency of 2 kHz (a typical modulation frequency for interrogation of an aerosol particle) the resonator tube is trimmed to a length of approximately 4.3 cm. This arrangement will set up a resonate standing-wave which effectively places a region of high acoustic energy at the active surface of each electret microphone 15. The signal from the microphone is fed to a lock-in amplifier tuned to the modulation frequency, f. The resultant amplified signal is proportional to the absolute absorption of the particle.

The wavelength of the tunable laser is then shifted slightly to the next wavelength of interest and the measurement is repeated until the desired absorption spectra, i.e., absorption versus laser wavelength, is completely recorded. This entire process is easily automated and can be repeated rapidly, i.e., charged particles are "grabbed", sampled, and released.

In addition to the uses mentioned above, the device described herein may also have application within the medical research community in which detailed information is needed on how certain forms of radiation affect single cell bacteria and their constitutes. Other applications, will be apparent to those skilled in the art.

Having thus shown and described what are at present considered to be preferred embodiments of the present invention, it should be noted that the same have been made by way of illustration and not limitation. Accordingly, all modifications, alterations and changes coming within the spirit and scope of the present invention are herein meant to be included. Many modifications of the preferred embodiments, which will still be within the spirit and scope of the invention will be apparent to those with ordinary skill in the art. In order to apprise of the various embodiments that may fall within the scope of the invention, the following claims are made.

We claim:

1. A single particle photoacoustic absorption spectrometer comprising:

- a particle trap for suspending a charged particle in free-space in a non-intrusive manner;
- a source of a modulated electromagnetic energy directed at the charged particle for rapid heating and cooling of the particle at the modulation frequency, resulting in an acoustic signal that is directly proportional to amount of energy absorbed by the particle;
- an acoustic transducer for detecting sound waves emitted by the suspended particle; and,
- a tuned resonant cavity for amplifying the acoustic wave.

2. The single particle absorption spectrometer of claim 1 wherein the radiation source comprises a laser.

3. The single particle absorption spectrometer of claim 2 wherein the laser is tunable.

4. The single particle absorption spectrometer of claim 2 wherein the particle trap comprises a spherical void electrodynamic trap.

5. The single particle absorption spectrometer of claim 4 wherein the acoustic transducer comprises a highly sensitive microphone.

6. The single particle absorption spectrometer of claim 5 wherein the microphone is an electret microphone.

7. The single particle absorption spectrometer of claim 6 further comprising a soundproof mounting assembly for isolation of the particle trap from ambient noise.

8. The single particle absorption spectrometer of claim 7 wherein the microphone is electrically shielded.

9. A method of single particle photoacoustic spectrometry comprising:

electrostatic charging of an aerosol particle;

trapping a single charged particle in free space via an electrodynamic trap;

irradiating the levitated particle with an electromagnetic radiation source modulated at an acoustic frequency; and measuring the sound emitted by the irradiated particle with an acoustic transducer.

10. The method of photoacoustic spectrometry of claim 9 further comprising re-measuring the intensity of the sound emitted by the particle after changing the wavelength of the radiation emitted from the electromagnetic source.

11. The method of caloric spectrometry of claim 10 wherein the acoustic transducer is positioned at a point of maximum acoustic energy density of a tuned resonant cylinder.

12. The method of photoacoustic spectrometry of claim 11 wherein the length of the resonant tube corresponds to the frequency of modulation of the electromagnetic source.

* * * * *